US00PP25421P2

(12) United States Plant Patent
Hartman

(10) Patent No.: US PP25,421 P2
(45) Date of Patent: Apr. 7, 2015

(54) ***CALADIUM* PLANT NAMED 'DESERT SUNSET'**

(50) Latin Name: *Caladium×hortulanum*
Varietal Denomination: Desert Sunset

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 129 days.

(21) Appl. No.: 13/986,553

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Desert Sunset', characterized by its upright and uniformly mounding plant habit; vigorous growth habit and rapid growth rate; lance-type leaves that are bronze salmon pink in color with darker-colored venation; and good landscape performance.

4 Drawing Sheets

Botanical designation: *Caladium×hortulanum.*
Cultivar denomination: 'DESERT SUNSET'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Desert Sunset'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Avon Park, Fla. of *Caladium×hortulanum* 'White Wonder', disclosed in U.S. Plant Pat. No. 21,044, as the female, or seed, parent with *Caladium×hortulanum* 'Twist and Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Desert Sunset'. These characteristics in combination distinguish 'Desert Sunset' as a new and distinct *Caladium* plant:

1. Upright and uniformly mounding plant habit.
2. Vigorous growth habit and rapid growth rate.
3. Lance-type leaves that are bronze salmon pink in color with darker-colored venation.
4. Good landscape performance.

Plants of the new *Caladium* differ primarily from plants of the female parent, 'White Wonder', in leaf color as plants of 'White Wonder' have leaves with white-colored background blushed with pink and distinct dark green-colored margins. In addition, plants of the new *Caladium* grow faster and produce finished plants one to two weeks earlier than plants of 'White Wonder'.

Plants of the new *Caladium* differ primarily from plants of the male parent, 'Twist and Shout', in leaf color as plants of 'Twist and Shout' have leaves that are olive green in color with coppery orange-colored blotches. In addition, plants of the new *Caladium* and 'Twist and Shout' differ in leaf petiole color as plants of 'Twist and Shout' have light green-colored leaf petioles.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differed primarily from plants of 'Florida Sweetheart' in the following characteristics:

1. Plants of the new *Caladium* were taller and more upright than plants of 'Florida Sweetheart'.
2. Plants of the new *Caladium* grew faster and produced finished plants about one to two weeks earlier than plants of 'Florida Sweetheart'.
3. Plants of the new *Caladium* and 'Florida Sweetheart' differed in leaf coloration as leaves of plants of 'Florida Sweetheart' had rose red-colored centers and dark green-colored margins.

Plants of the new *Caladium* can be compared to plants of *Caladium×hortulanum* 'White Delight', disclosed in U.S. Plant Pat. No. 21,216. In side-by-side comparisons, plants of the new *Caladium* differed primarily from plants of 'White Delight' in the following characteristics:

1. Plants of the new *Caladium* grew faster and produced finished plants about one to two weeks earlier than plants of 'White Delight'.
2. Plants of the new *Caladium* had broader leaves than plants of 'White Delight'.
3. Plants of the new *Caladium* and 'White Delight' differed in leaf coloration as leaves of plants of 'White Delight' were white to grey-green in color with white-colored main veins and green-colored or speckled margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Desert Sunset' in a 15-cm container and grown in a shadehouse.

The photograph at the top of the second sheet is a comparison view of typical plants of 'Desert Sunset' grown in 15-cm containers; the plant on the left has not had its tuber de-eyed and the plant on the right has had its tuber de-eyed prior to planting.

The photograph at the bottom of the second sheet is a close-up view of typical freshly-harvested tubers and roots of 'Desert Sunset'.

The photograph at the top of the third sheet is a close-up view of typical plants of 'Desert Sunset' grown in an open field.

The photograph at the bottom of the third sheet is a close-up view of typical inflorescences of 'Desert Sunset'.

The photograph at the top of the fourth sheet is a comparison view of typical potted plants of 'Florida Sweetheart' (left), 'Desert Sunset' (center) and 'White Delight' (right).

The photograph at the bottom of the fourth sheet is a comparison view of typical potted plants of the female parent, 'White Wonder' (left), 'Desert Sunset' (center) and the male parent, 'Twist and Shout' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were six weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Desert Sunset'.

Parentage:

*Female, or seed, parent.*—*Caladium×hortulanum* 'White Wonder', disclosed in U.S. Plant Pat. No. 21,044.

*Male, or pollen, parent.*—*Caladium×hortulanum* 'Twist and Shout', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate to elliptic in shape. Height: About 3 cm to 3.4 cm. Diameter: About 4 cm to 4.3 cm. Segment height: About 1.9 cm to 2.3 cm. Segment diameter: About 2.2 cm to 2.7 cm. Texture: Thick, starchy; somewhat brittle. Color: Epidermis, freshly-harvested: Close to 199C to 199D and darker than N199B. Epidermis, dried: Close to 200A to 200B. Cortical tissue: Close to 155A and 8D. Axillary buds: Close to 36C to 36D. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Upright and uniformly mounding plant habit; vigorous and dense growth habit; rapid growth rate, potted plants in finished or saleable form in about six to seven weeks after planting tubers; leaf petioles and leaves arise from one or more growing points on tubers; petioles mostly upright and arching outwardly with development.

*Plant height, from soil level to top of foliar plane, shadehouse-grown potted plants.*—About 23 cm to 27 cm.

*Plant height, from soil level to top of inflorescences, shadehouse-grown potted plants.*—About 33 cm.

*Plant diameter or spread, shadehouse-grown potted plants.*—About 40 cm to 43 cm.

*Number of clumps per plant, shadehouse-grown potted plants.*—About three from de-eyed tubers.

*Cataphylls, shadehouse-grown potted plants.*—Length: About 5 cm to 8 cm. Width: About 1.1 cm to 2 cm. Shape: Wedge-shaped. Apex: Acute to acuminate. Base: Sheathing the stem. Color, outer surface: Close to 147D and 145D tinged with close to 146A to 146B and N170D; stippled, streaked and tessellated with close to 147A; with development, color becoming closer to 200C stained with close to 187B to 187C. Color, inner surface: Close to N155C; outer surface colors and patterns visible.

Foliage description:

*Arrangement and type.*—Alternate; simple; lance-type.

*Length, shadehouse-grown potted plants.*—About 16 cm to 24 cm.

*Width, shadehouse-grown potted plants, flattened.*—About 13 cm to 17 cm.

*Shape.*—Ovate, broadly ovate to somewhat deltoid.

*Apex.*—Acuminate.

*Base.*—Sagittate to sagittate peltate.

*Margin.*—Entire; wavy with broad undulations.

*Texture, upper surface*.—Smooth, glabrous; leathery; dull sheen.

*Texture, lower surface*.—Smooth, glabrous; glaucous.

*Venation pattern*.—Pinnate.

*Color, shadehouse-grown potted plants*.—Developing leaves, upper surface: Background color: Central areas, close to 183D and 182B; marginal areas, close to 178A and 176C. Basal notch: Close to 187A. Venation: Close to 176B tinged with close to 183A. Developing leaves, lower surface: Background color: Central areas, close to 182D; marginal areas, close to 191A. Basal notch: Close to 187B to 187C. Midvein: Close to 147B tinged with close to 162D. Lateral venation: Close to 191A and 147B. Fully expanded leaves, upper surface: Background color: Central areas, close to 182C to 182D tinged with close to N34C; marginal areas, close to 183C, 185A and 182C. Basal notch: Close to 187B and 147C. Venation: Close to 185A and 183B. Fully expanded leaves, lower surface: Background color: Close to 182C to 182D and 180D. Basal notch: Close to 187B to 187C. Venation: Close to 148C to 148D; adjacent to venation, close to 145C to 145D.

*Petiole*.—Aspect: Initially upright and straight; with development, leaning outwardly; flexible. Length, shadehouse-grown potted plants: About 17 cm to 22 cm. Diameter, distal, shadehouse-grown potted plants: About 3.5 mm to 4 mm. Diameter, proximal, shadehouse-grown potted plants: About 7 mm to 9 mm. Color, shadehouse-grown potted plants: Just below leaf and petiole junction, variably tinged with close to N170D and 177D; proximally, between 147C and 146C tinged with close to N170D and faintly stippled, streaked and tessellated with close to 147B to 147C. Wing length, shadehouse-grown potted plants: About 4.3 cm to 5.2 cm. Wing diameter, shadehouse-grown potted plants: About 6 mm to 10 mm. Wing color, shadehouse-grown potted plants, outer surface: Close to 147D and 145D tinged with close to 146A to 146B and stippled, streaked and tessellated with close to 147A. Wing color, shadehouse-grown potted plants, inner surface: Close to N155C; outer surface colors and patterns visible.

Inflorescence description: Inflorescences observed on eight week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; sweet jasmine-like fragrance with camphor-like notes.

*Natural flowering season and flower longevity*.—Plants of the new *Caladium* typically flower during the spring or early summer in central Florida; flowers develop about eight weeks after growth commences; inflorescences last about three days before fading; inflorescences persistent.

*Spathe*.—Length, overall: About 10 cm. Length, distal open portion: About 6.5 cm. Length, proximal closed portion: About 3.5 cm. Width, distal open portion: About 4.5 cm. Width, at constriction: About 9 mm. Width, proximal closed portion: About 2.4 cm. Shape: Ovate to somewhat obovate. Apex: Acuminate. Base: Tapering to the peduncle. Margin: Entire. Texture, front and rear surfaces: Smooth, glabrous. Color, front surface: Distal open portion: Close to 155A and 158D; with development, color becoming closer to 199C. Proximal closed portion: Close to 138C and 147C; towards the base, tinged with close to 187A; color does not change with development. Color, rear surface: Distal open portion: Close to 159D, 160D and 145D. Proximal closed portion: Between 147B and 146B.

*Spadix*.—Length: About 8.8 cm. Length, male flower zone: About 6.5 cm. Length, sterile zone: Less than 1 cm. Length, female flower zone: About 2.3 cm. Diameter, male flower zone: About 1 cm. Diameter, sterile flower zone: About 7 mm. Diameter, female flower zone: About 9 mm. Shape: Columnar, spindle-shaped. Apex: Bluntly acute. Base: Obtuse. Aspect: Upright. Color, mature, male zone: Close to 13D. Color, mature, sterile zone: Close to 161D. Color, mature, female zone: Close to 8C to 8D. Male flowers: Quantity per spadix: About 183. Shape: Obovate. Height: About 3 mm. Diameter: About 3 mm. Pollen amount: Moderate. Pollen color: Close to 4C to 4D. Female flowers: Quantity per spadix: About 140. Shape: Obovate. Height: About 3 mm. Diameter: About 2 mm. Stigma color: Close to 158D. Ovary color: Close to 155C.

*Scape*.—Length: About 23 cm. Diameter: About 6 mm. Strength: Sturdy; flexible. Aspect: Mostly erect. Texture: Smooth, glabrous; glaucous. Color: Between 147B and 148A faintly streaked with close to 147A.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Desert Sunset' as illustrated and described.

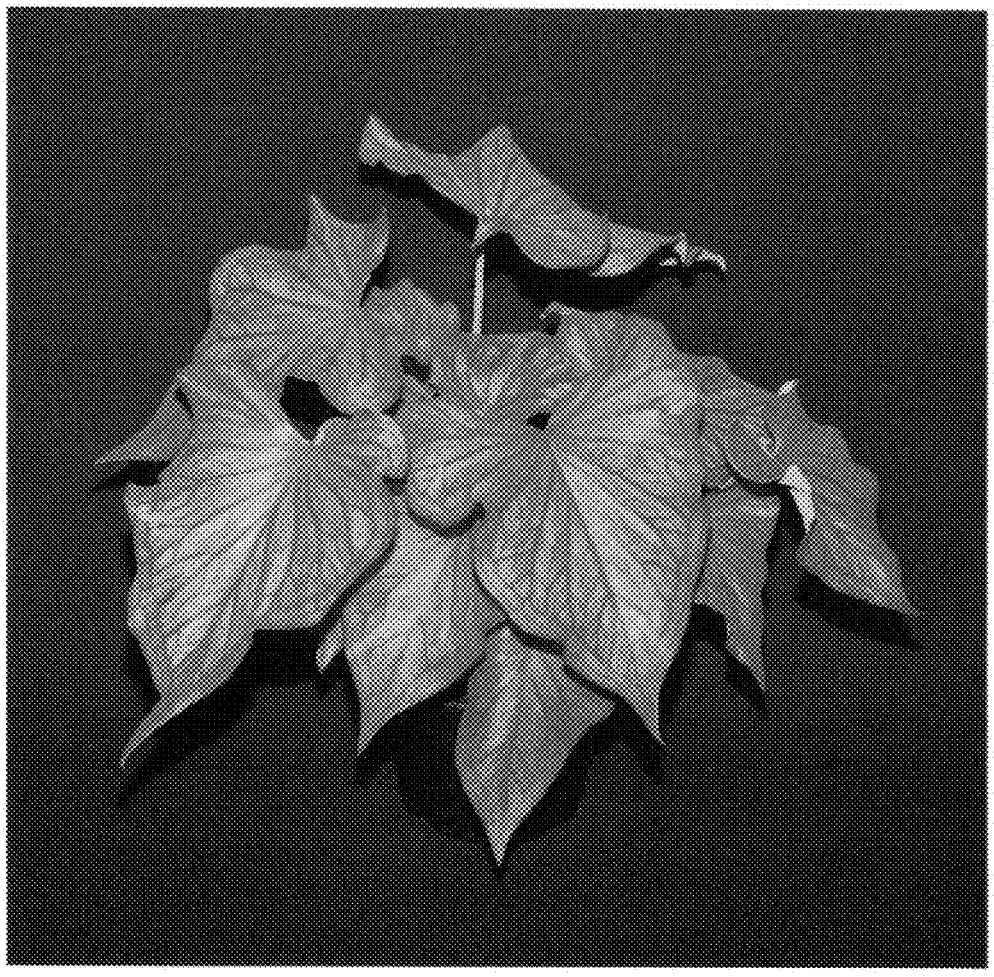

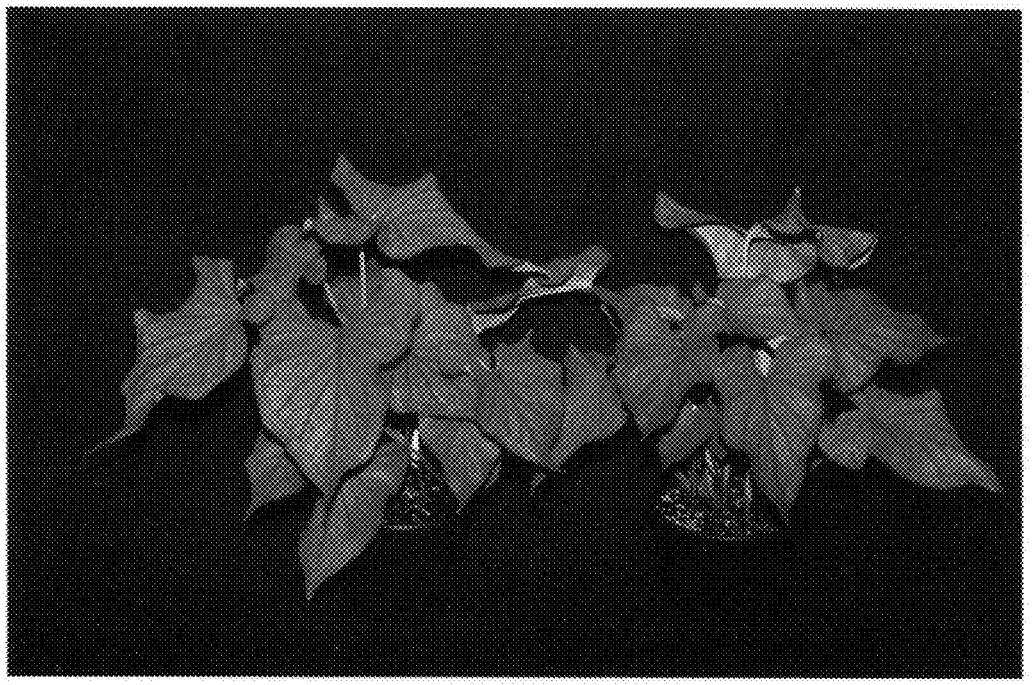
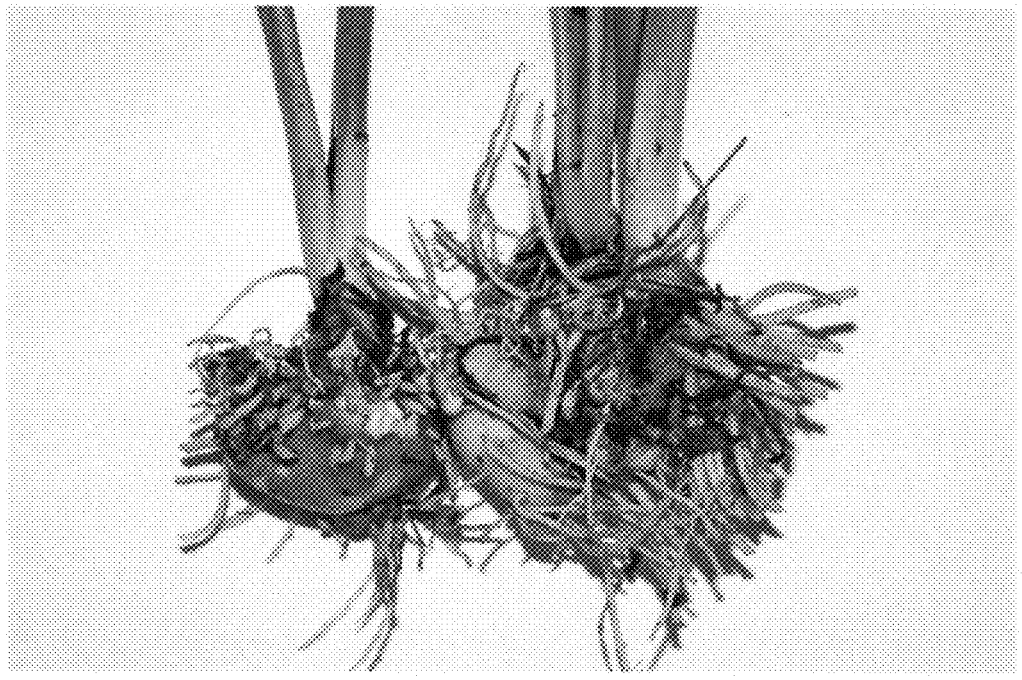

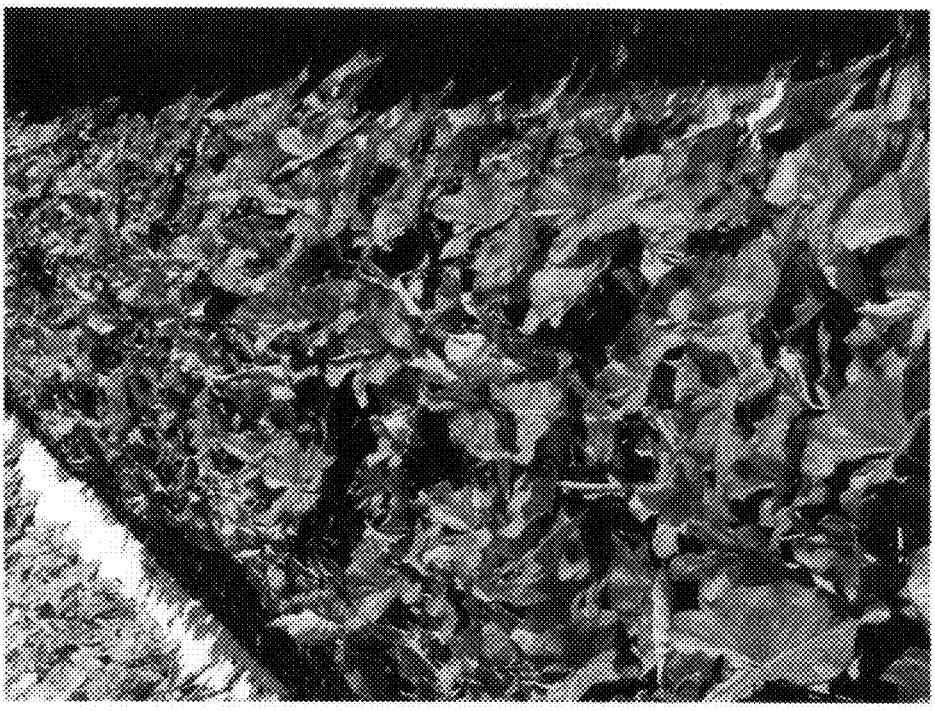
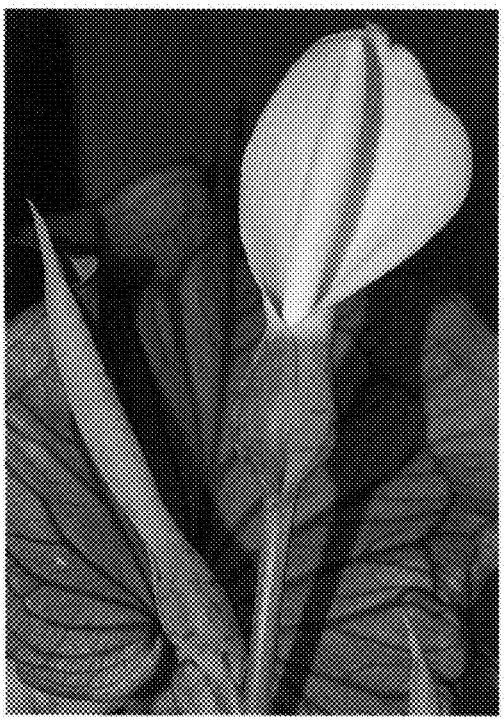

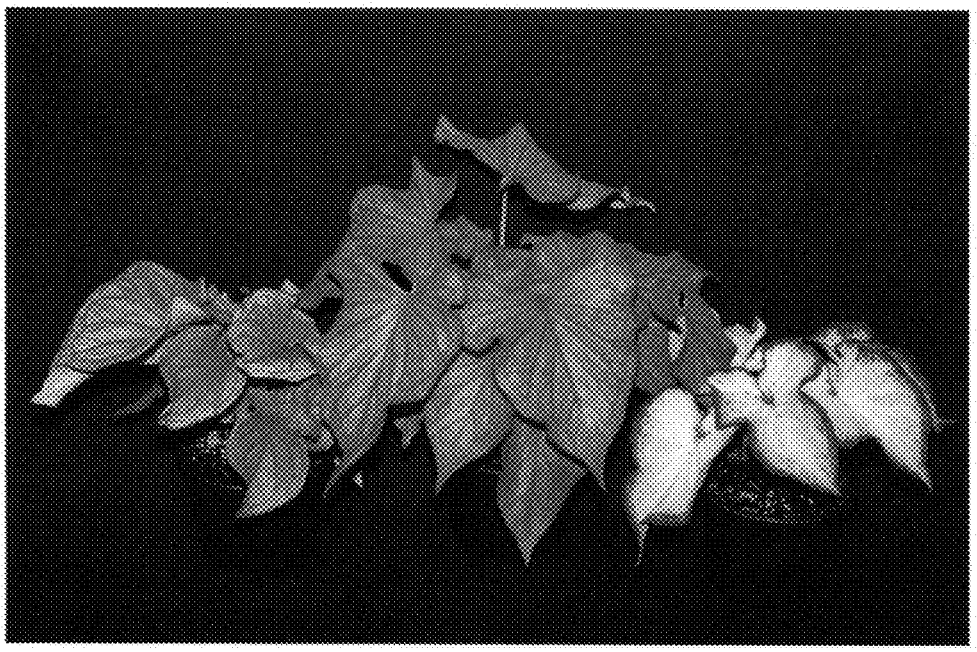
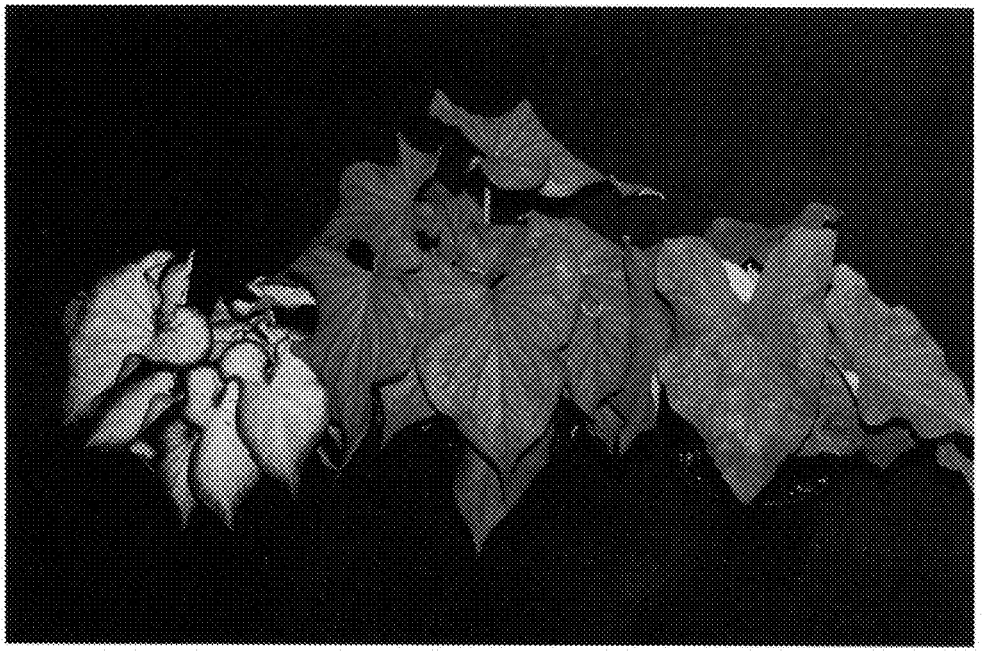

* * * * *